US 7,067,513 B1
Jun. 27, 2006

(54) PHENYLPIPERAZINES

(75) Inventors: Roelof Van Hes, Weesp (NL);
Johannes A. M. Van der Heijden, Weesp (NL); Cornelis G Kruse, Weesp (NL); Jacobus Tipker, Weesp (NL); Martinus T. M Tulp, Weesp (NL); Gerben M Visser, Weesp (NL); Bernard J Van Vliet, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 29 days.

This patent is subject to a terminal disclaimer.

(21) Appl. No.: 10/069,256

(22) PCT Filed: Aug. 22, 2000

(86) PCT No.: PCT/EP00/08190

§ 371 (c)(1),
(2), (4) Date: Sep. 23, 2002

(87) PCT Pub. No.: WO01/14330

PCT Pub. Date: Mar. 1, 2001

(30) Foreign Application Priority Data

Aug. 23, 1999 (EP) .................................. 99202710
Aug. 23, 1999 (NL) .................................. 1012888

(51) Int. Cl.
*A61K 31/536* (2006.01)
*A61K 31/5415* (2006.01)
*C07D 401/14* (2006.01)
*C07D 413/14* (2006.01)
*C07D 417/14* (2006.01)

(52) U.S. Cl. .............................. 514/224.2; 514/230.5; 514/253.06; 514/253.07; 514/212.07; 514/217.05; 514/254.02; 514/254.06; 514/254.09; 514/254.11; 540/523; 540/593; 544/52; 544/105; 544/363; 544/368; 544/373; 544/370; 544/376; 544/51; 544/377

(58) Field of Classification Search ............ 544/51–52, 544/105, 363; 514/224.2, 230.5, 253.06, 514/253.07
See application file for complete search history.

(56) References Cited

U.S. PATENT DOCUMENTS

| 5,002,948 | A | 3/1991 | Perregaard et al. |
|---|---|---|---|
| 5,242,925 | A | 9/1993 | Böttcher et al. |
| 5,314,896 | A | 5/1994 | Caprathe et al. |
| 5,532,241 | A | 7/1996 | Böttcher et al. |
| 5,576,321 | A | 11/1996 | Krushinski, Jr. et al. |
| 5,693,655 | A | 12/1997 | Böttcher et al. |
| 6,214,829 | B1 * | 4/2001 | Feenstra et al. ....... 514/253.06 |
| 6,251,908 | B1 | 6/2001 | Böttcher et al. |
| 6,262,087 | B1 | 7/2001 | Perregaard et al. |
| 6,352,988 | B1 | 3/2002 | Perregaard et al. |
| 6,391,896 | B1 | 5/2002 | Van Hes et al. |
| 6,552,044 | B1 | 4/2003 | Perregaard et al. |
| 6,828,325 | B1 | 12/2004 | Feenstra et al. |
| 2001/0020095 | A1 | 9/2001 | Perregaard et al. |
| 2001/0021777 | A1 | 9/2001 | Perregaard et al. |
| 2004/0024207 | A1 * | 2/2004 | Bakker ........................ 544/105 |

FOREIGN PATENT DOCUMENTS

DE          4127849 A1 *   2/1993

(Continued)

OTHER PUBLICATIONS

Robichaud et al. Annual Reports in Medicinal Chemistry, vol. 35, p. 11-20 (2000).*

(Continued)

*Primary Examiner*—Emily Bernhardt
(74) *Attorney, Agent, or Firm*—Finnegan, Henderson, Farabow, Garrett & Dunner LLP

(57) ABSTRACT

The invention relates to a novel group of phenylpiperazines having interesting pharmacological properties such as a high affinity for the dopamine $D_2$ receptor and/or the serotonin reuptake site, and the ability to treat conditions related to disturbances in the dopaminergic and/or the serotonergic systems such as aggression, anxiety disorders, autism, vertigo, depression, disturbances of cognition, disturbances of memory, Parkinson's disease, schizophrenia, and psychotic disorders.

The invention relates to a group of novel phenylpiperazine derivatives of the formula (I):

wherein:
X is a group of formula 1, 2, 3, 4, 5, 6, or 7 as defined in the text,
m has the value 2 to 6;
n has the value 0–2;
$R_5$ and $R_6$ are independently H or alkyl (1–3C); or $R_5+R_6$ represent a group —$(CH_2)$—$_p$ wherein p has the value 3–5, and
$R_7$ is alkyl (1–3C), alkoxy (1–3C), halogen or cyano; or $R_6+R_7$ ($R_7$ at position 7 of the indole group) represent a group —$(CH_2)_q$ wherein q has the value 2–4,
and salts thereof.

7 Claims, No Drawings

FOREIGN PATENT DOCUMENTS

| | | | |
|---|---|---|---|
| DE | 4333254 A1 * | 4/1995 |
| DE | 44 14 113 A1 | 10/1995 |
| DE | 19730989 A1 * | 1/1999 |
| EP | 376607 * | 7/1990 |
| EP | 0 722 941 A2 | 7/1996 |
| GB | 1075156 | 7/1967 |
| HU | 218 935 B | 10/1995 |
| WO | WO 97/17343 | 5/1997 |
| WO | WO 98/28293 | 7/1998 |
| WO | WO 99/03855 | 1/1999 |
| WO | 99/05140 * | 2/1999 |
| WO | WO 99/67237 | 12/1999 |
| WO | PCT/EP00/08190 | 2/2001 |
| WO | WO 03/068207 A2 | 8/2003 |

OTHER PUBLICATIONS

TenBrink et al. Annual Reports in Medicinal Chemistry, vol. 29, p. 43-51 (1994).*

Jones et al. Pharmacology,Biochemistry and Behavior, vol. 71, p. 555-568 (2002).*

* cited by examiner

PHENYLPIPERAZINES

The invention relates to a group of novel phenylpiperazine derivatives of the formula (I):

(I)
X—N(piperazine)N—(CH$_2$)$_m$—[indole with R$_5$, R$_6$, (R$_7$)$_n$]

wherein:
X is 1) a group of the formula (1)
[structure with S$_1$, S$_2$, S$_3$, S$_4$, S$_5$, Y]

wherein
S$_1$ is hydrogen or halogen,
S$_2$ and S$_3$ are independently hydrogen, alkyl (1–6C), phenyl or benzyl,
S$_4$ represents two hydrogen atoms or an oxo group,
S$_5$ is H or alkyl (1–4C), and
Y is CH$_2$, O or S, or 2) a group of the formula (2)
[structure with CH$_2$OR, S$_1$]

wherein S$_1$ has the above meaning and R is H, alkyl (1–4C), alkoxyalkyl (2–6C), alkenyl (2–4C) or alkynyl (2–4C), or 3) a group of the formula (3)
[structure with HN, Z, O, S$_1$]

wherein S$_1$ has the above meaning and Z is CH$_2$, O or NH, or 4) a group of the formula (4)
[quinoline structure with S$_1$]

wherein S$_1$ has the above meaning, or 5) a group of the formula (5)
[structure with A, O, S$_1$]

wherein S$_1$ has the above meaning and A is O or NH, linked to the piperazine ring with position 5 or 8, or 6) a group of the formula (6)
[benzazepine structure with S$_6$, S$_7$, HN, S$_1$]

wherein S$_1$ has the above meaning and S$_6$ and S$_7$ represent hydrogen atoms or an oxo group, or 7) a group of the formula (7)
[structure with P, T, Q, S$_1$]

wherein one of the dotted lines can represent a double bond, S$_1$ has the above meaning, and
P, T, and Q are independently nitrogen or NH
or P and T are independently nitrogen or NH and Q is CH or CH$_2$
or P and Q are independently nitrogen or NH and T is CH, CH$_2$, C—CH$_3$ or CH—CH$_3$
or P is nitrogen or NH, and T and Q are independently CH or CH$_2$
or P is nitrogen or NH, T is CH or CH$_2$ and Q is sulphur m has the value 2 to 6;

n has the value 0–2;

$R_5$ and $R_6$ are independently H or alkyl (1–3C); or $R_5+R_6$ represent a group —$(CH_2)$—$_p$ wherein p has the value 3–5, and $R_7$ is alkyl (1–3C), alkoxy (1–3C), halogen or cyano; or $R_6+R_7$ ($R_7$ at position 7 of the indole group) represent a group —$(CH_2)_q$ wherein q has the value 2–4, and salts thereof, which show high affinity for the dopamine $D_2$-receptor and are good serotonin reuptake inhibitors (SRI's).

Preferred compounds of the invention are compounds having formula (I) wherein X represents a group of the formula (1), (2) or (3), wherein the symbols have the meanings given above and the salts thereof.

Especially preferred are compounds having formula (I) wherein X is the group with the formula (1) wherein $S_1$=H, $S_2$=$CH_3$, $S_3$=H, $S_4$=oxo, $S_5$=H and Y is oxygen, m is 3, $R_5$=$R_6$=hydrogen, n is 0 or 1 and $R_7$ is 5-fluoro, and the salts thereof.

It has been found that the compounds according to the invention show high affinity for both the dopamine $D_2$ receptor and the serotonin reuptake site. This combination is useful for the treatment of schizophrenia and other psychotic disorders which enables a more complete treatment of all disease symptoms (e.g. positive symptoms and negative symptoms).

However, some of the compounds having formula (I) show (partial) agonist activity at dopamine receptors making them particularly suitable for the treatment of Parkinson's disease.

The compounds show activity as antagonists at dopamine $D_2$ receptors as they potentially antagonize apomorphine-induced climbing behaviour in mice. The compounds also show activity as inhibitors of serotonin reuptake, as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61–67) and antidepressants or anxiolytics (e.g. suppression of stress-induced vocalization; van der Poel et al., Psychopharmacology, 1989, 97: 147–148).

In contrast to clinically relevant dopamine $D_2$ receptor antagonists the described compounds have a low propensity to induce catalepsy in rodents and as such are likely to induce less extrapyramidal side effects than existing antipsychotic agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory, Parkinson's disease, and in particular schizophrenia and other psychotic disorders.

Pharmacologically acceptable acids with which the compounds of the invention can form suitable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methanesulphonic acid and naphthalene sulphonic acid.

When the compounds comprise a centre of chirality both the racemic mixture and the individual enantiomers belong to the invention.

The compounds and their acid addition salts can be brought into forms suitable for administration by means of suitable processes using auxiliary substances such as liquid and solid carrier materials.

The compounds having formula (I) can be prepared by reaction of a compound of the formula

under basic conditions with a compound of the formula

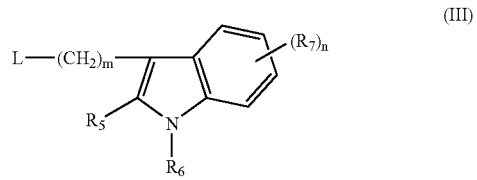

in which formulae the symbols have the meanings given above, and L is a so-called leaving group such as a halogen atom or a mesylate group.

The piperazine compounds having formula (II) can be obtained as described in EP 0138280, EP 0189612 and/or EP 0900792, or in an analogous manner.

The preparation of the piperazines having formula (II) can be carried out as indicated in schemes (i)–(iv) below. Some of the routes result in optically pure piperazine derivatives.

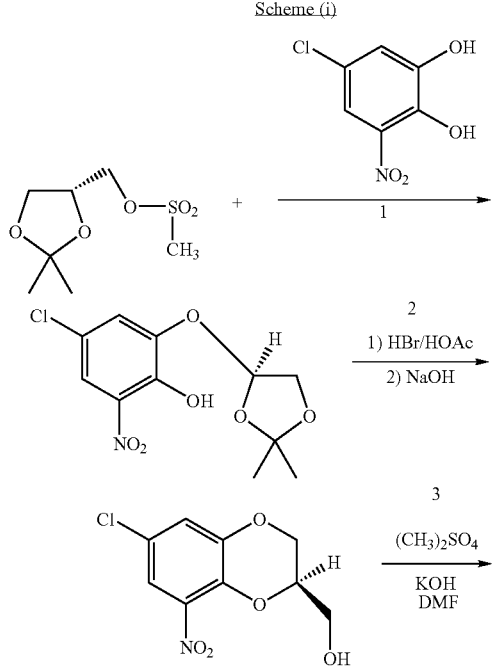

Scheme (i)

-continued
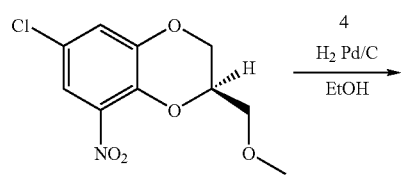
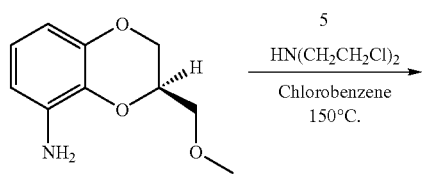
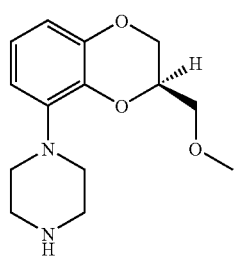
= a,i
Scheme (ii)
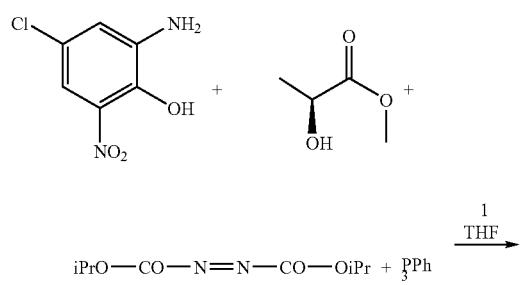
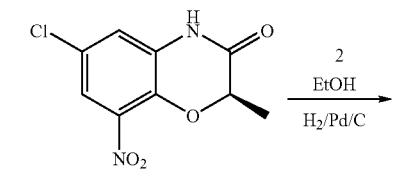
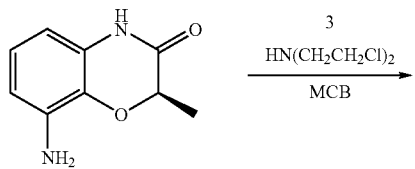
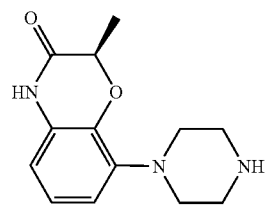
= b,ii
Scheme (iii)
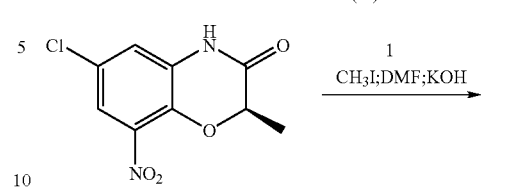
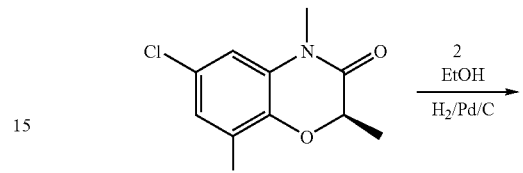
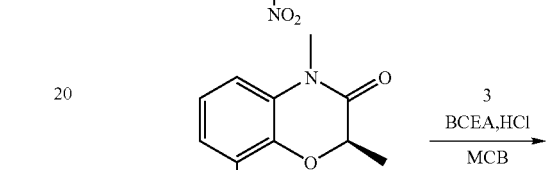
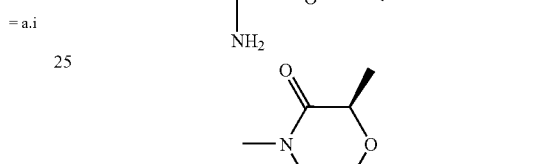
= c,iii
Scheme (iv)
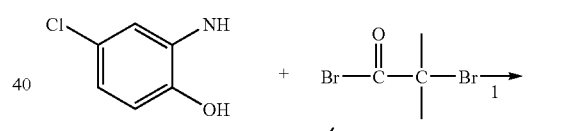
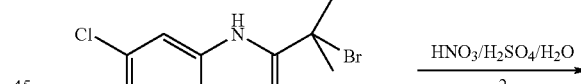
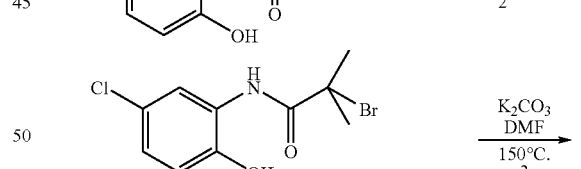
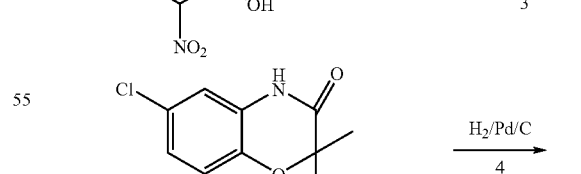
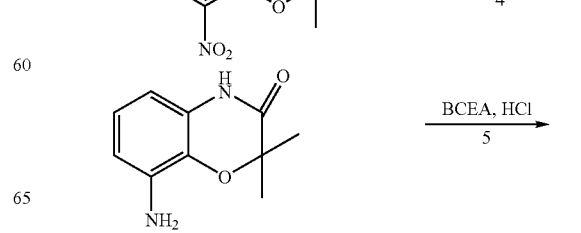

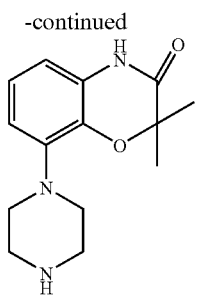

=d, iv

The starting compounds having formula (III) can be prepared according to methods known for analogues compounds, as described for example in Organic Process Res. and Dev. 1997 (1), 300–310.

The invention will now be illustrated by means of the following Examples:

EXAMPLE 1

Preparation of Compound a,i (See Scheme i)

Step 1 (scheme i): To a solution of chloronitrocatechol (6.45 g, 34 mmol) in dry DMSO (50 ml) was added powdered NaOH (2.72 g, 68 mmol). After stirring for 30 minutes a solution was added of R-glycerolketal mesylate (8.0 g, 38 mmol) in DMSO (20 ml) and this mixture was heated at 80° C. during 24 hours. After cooling to room temperature the reaction mixture was poured into water (200 ml), acidified with 1 N HCl and extracted with methyl t-butylether. The organic fraction was washed with water and dried on MgSO$_4$. After removal of the drying agent and the solvent in vacuo, the resulting oil was subjected to flash chromatografy (SiO$_2$, eluent PE/aceton=3/1). Yield 9.29 g (90%) of the S-ketal.

Step 2 (scheme i): To a solution of the S-ketal (31 g, 102 mmol) in acetic acid (120 ml) was added 35% HBr in acetic acid (80 ml) and this mixture was rotated for 2 hours on a rotavapor in a waterbath of 50° C. The reaction mixture was diluted with ethanol (96%, 250 ml), cooled in a salt/ice mixture and then NaOH (50% in water, 250 ml) was added slowly, keeping the temperature below 15° C. After adding ethanol (250 ml) and water (250 ml) the reaction mixture was stirred at room temperature for 16 hours. Then concentrated HCl (about 300 ml) and water were added and the mixture extracted with ethyl acetate. After washing the organic fraction with 5% NaHCO$_3$ (4×500 ml), the solvent was removed in vacuo and the resulting oil was subjected to flash chromatografy (SiO$_2$, eluent PE/aceton=3/1). Yield 20.5 g (81%) of the R-benzodioxane as a yellow oil.

Step 3 (scheme i): To a solution of R-benzodioxane (20 g, 81 mmol) in DMF (200 ml) was added KOH (4.56 g, 81 mmol). After cooling the red solution in ice/aceton dimethyl sulfate (23 ml) was added and the reaction mixture was stirred for 1.5 hours at room temperature. Then more KOH (4.56 g, cooling) was added and the mixture was stirred at room temperature for 16 hours. After adding water (700 ml), the product was extracted with ethyl acetate. The ethyl acetate was removed in vacuo and the resulting oil was subjected to flash chromatografy (SiO$_2$, eluent PE/aceton=4/1) yielding R-methoxymethylbenzodioxane (12.3 g, 58%) as a yellow oil. $[\alpha]_D^{25}$=−97° (methanol).

Step 4 (scheme i): To a solution of R-methoxymethyl-benzodioxane (5 g, 19 mmol) in ethanol (100 ml) and ethyl acetate (50 ml) was added a catalytic amount of 10% Pd/C and the solution was shaken under atmospheric H$_2$ pressure at room temperature. After the calculated amount of H$_2$ was taken up by the reaction mixture, the catalyst was removed by filtration and the filtrate was concentrated in vacuo. Yield 3.7 g (100%) of the corresponding anilino-compound.

Step 5 (scheme i): The anilino-compound (4 g, 2 mmol) and BCEA, i.e. HN(CH$_2$CH$_2$Cl)$_2$.HCl (3.7 g, 2 mmol) were dissolved in chlorobenzene (100 ml). The mixture was heated to 150° C. for 16 hours, concentrated in vacuo and purified by flash chromatografy (SiO$_2$, dichloromethane/methanol/ammonium hydroxide=92/7.5/0.5). Yield 3.67 g (68%) of the piperazine a,i.

EXAMPLE 2

Preparation of Compound No. 126

The route is described above, i.e. reaction of compound (II) with compound (III). The mesylates of formula (III) were prepared from the corresponding alcohols by standard procedures, e.g. with MsCl/Et$_3$N.

A mixture of the piperazine a,i (3,6 g, 13,6 mmol), the 5-fluoro indole-mesylate (4,1 g, 15,1 mmol), triethylamine (2 ml) and a catalytic amount of KI in CH$_3$CN (100 ml) was heated under reflux during 18 hours after which the reaction mixture was concentrated in vacuo and purified by chromatografy (SiO$_2$, dichloromethane/methanol/ammonium hydroxide=92/7.5/0.5). Yield 3,77 of the free base (oil). The free base was dissolved in ethanol and 1 equivalent of fumaric acid in ethanol was added. After removal of the solvent compound no. 126 was obtained (4,3 g, 57%). $[\alpha]_D^{25}$=−2° (methanol)

EXAMPLE 3

Preparation of Compound b,ii (See Scheme ii)

Step 1 (scheme ii): A solution of the aminophenol (37.3 g, 198 mmol), S-lactic acid methyl ester (20 ml) and triphenylphosphine (58 g, 220 mmol) in THF (2000 ml) was cooled in ice/salt (temperature<10° C.). Then a solution of azodicarboxic acid ester (DIAD, 43 ml, 218 mmol) in THF (400 ml) was added slowly. After stirring at room temperature for 18 hours the reaction mixture was concentrated in vacuo and ethanol (500 ml) and 36% HCl (125 ml) were added to the residue. The mixture was heated to 100° C. (development of gas). After cooling the compound was isolated by filtration and washed with 96% ethanol (about 100 ml). Yield 42 g (87%).

Step 2 (scheme ii): This step is similar to step 4 described in scheme i.

Step 3 (scheme ii): This step is similar to step 5 described in scheme i, resulting in the formation of the piperazine b,ii.

EXAMPLE 4

Preparation of Compound No. 89

The route is described above, i.e. reaction of compound (II) with compound (III). The reaction is carried out as described in example 2, starting with the piperazine b,ii. Yield 58% of compound no. 89, $[\alpha]_D^{25}$=−24° (methanol).

EXAMPLE 5

Preparation of Coumpound c,iii (See Scheme iii)

Step 1 (scheme iii): A solution of the benzomorpholinone (10 g, 41 mmol; see scheme ii, step 1) and powdered KOH (2.3 g, 41 mmol) in DMF (100 ml) was cooled in ice (temperature<10° C.). After adding 1 equivalent of MeI (2.55 ml, 41 mmol) the reaction mixture was stirred at room temperature for about 1.5 hours and then poured into water. The precipitate was filtered off, washed with water and dried. Yield 10 g (95%) of the NCH$_3$-compound, mp. 191–192; $[\alpha]_D^{25}$=+7.5° (in THF)

Step 2 (scheme iii): This step is similar to step 4 described in scheme i.

Step 3 (scheme iii): This step is similar to step 5 described in scheme i, resulting in the formation of the piperazine c,iii.

EXAMPLE 6

Preparation of Compound No. 121

The route is described above, i.e. reaction of compound (II) with compound (III). The reaction is performed as described in example 2, starting with the piperazine c,iii. Yield 44% of compound no. 121, $[\alpha]_D^{25}$=−28° (methanol).

EXAMPLE 7

Preparation of Compound d,iv (See Scheme iv)

Step 1 (scheme iv): Pyridine (81 ml, 1 mol) was added to a solution of 2-hydroxy-5-chloroaniline (143.5 g, 1 mol) in dry CH$_2$Cl$_2$. The mixture was cooled in ice (temperature<10° C.) and then a solution of 2-bromo-2-methyl-propionylbromide (163 ml, 1 mol) in CH$_2$Cl$_2$ (100 ml) was added slowly. The mixture was stirred at room temperature for 18 hours and was poured into CH$_2$Cl$_2$ (5000 ml) and water (2000 ml). The organic layer was washed with water, dried and concentrated in vacuo till about 1 liter. The precipitate was filtered off, washed with CH$_2$Cl$_2$ and dried. Yield 231 g (79%) of the bromocompound, mp. 172° C.

Step 2 (scheme iv): To a suspension of the bromocompound (60 g, 205 mmol) in water (95 ml) was added slowly under ice cooling concentrated sulfuric acid (7 ml) followed by 70% HNO$_3$ (16 ml) and stirring was continued for 2 hours at room temperature. After cooling in ice water the precipitate was filtered off, washed with water and purified by chromatografy (SiO$_2$, methyl t-butylether). Yield 49 g (71%) of the nitrocompound.

Step 3 (scheme iv): To a solution of the nitrocompound (49 g, 145 mmol) in DMF (500 ml) was added K$_2$CO$_3$. This mixture was heated for one hour at 150° C., then cooled and poured into a mixture water/ethyl acetate. The organic fraction was washed with sodium bicarbonate (5% in water) HCl (2N) and water respectively. The solvent was removed in vacuo and the residue was purified by flash chromatografy (SiO$_2$, methyl t-butylether/PE=1/1). Yield 23 g (62%).

Step 4 (scheme iv): This step is similar to step 4 described in scheme i.

Step 5 (scheme iv): This step is similar to step 5 described in scheme i, leading to the formation of the piperazine d,iv.

EXAMPLE 8

Preparation of Compound No. 115

The route is described above, i.e. reaction of compound (II) with compound (III). The reaction is performed as described in example 2, starting with the piperazine d,iv. Yield 20% of compound no. 115.

The compounds listed in the following tables have been prepared according to the method of the above examples.

| Comp. no | X | m | Y | R$_5$ | R$_6$ | (R$_7$)n | R | Z | A | S$_6$ + S$_7$ | P | T | Q | Remarks |
|---|---|---|---|---|---|---|---|---|---|---|---|---|---|---|
| 1 | form | 2 | 3 | — | H | H | H | 2-CH$_2$OH | — | — | — | — | — | — | S$_1$ = H |
| 2 | | 1 | 3 | CH$_2$ | H | H | H | — | — | — | — | — | — | — | S$_1$–S$_5$ = H |
| 3 | | 3 | 3 | — | H | H | H | — | O | — | — | — | — | — | S$_1$ = H |
| 4 | | 3 | 4 | — | H | H | H | — | O | — | — | — | — | — | S$_1$ = H |
| 5 | | 3 | 4 | — | H | H | H | — | O | — | — | — | — | — | S$_1$ = H |
| 6 | | 3 | 3 | — | H | CH$_3$ | H | — | O | — | — | — | — | — | S$_1$ = H |
| 7 | | 2 | 3 | — | H | H | H | 3-CH$_2$OH | — | — | — | — | — | — | S$_1$ = H |
| 8 | | 1 | 3 | O | H | H | H | — | — | — | — | — | — | — | S$_4$ = oxo, S$_1$ = S$_2$ = S$_3$ = S$_5$ = H |
| 9 | | 1 | 3 | O | H | H | H | — | — | — | — | — | — | — | S$_1$–S$_5$ = H |
| 10 | | 4 | 3 | — | H | H | H | — | — | — | — | — | — | — | S$_1$ = H |
| 11 | | 1 | 3 | CH$_2$ | H | H | H | — | — | — | — | — | — | — | S$_1$, S$_3$–S$_5$ = H; S$_2$ = CH$_3$ |
| 12 | | 3 | 3 | — | H | —(CH$_2$)$_3$— | | — | O | — | — | — | — | — | S$_1$ = H |
| 13 | | 2 | 3 | — | H | H | H | 3-CH$_2$OH | — | — | — | — | — | — | S$_1$ = H* |
| 14 | | 1 | 3 | CH$_2$ | —(CH$_2$)$_4$— | | H | — | — | — | — | — | — | — | S$_1$–S$_5$ = H |
| 15 | | 3 | 3 | — | H | H | 5-OCH$_3$ | — | O | — | — | — | — | — | S$_1$ = H |
| 16 | | 1 | 3 | CH$_2$ | CH$_3$ | H | 5-Cl | — | — | — | — | — | — | — | S$_1$–S$_5$ = H |
| 17 | | 3 | 3 | — | CH$_3$ | H | 5-Cl | — | O | — | — | — | — | — | S$_1$ = H |
| 18 | | 1 | 3 | CH$_2$ | H | H | 5-Br | — | — | — | — | — | — | — | S$_1$–S$_5$ = H |
| 19 | | 3 | 3 | — | H | H | 5-Br | — | O | — | — | — | — | — | S$_1$ = H |
| 20 | | 1 | 2 | CH$_2$ | H | H | H | — | — | — | — | — | — | — | S$_1$–S$_5$ = H |
| 21 | | 1 | 3 | CH$_2$ | H | H | 5-F | — | — | — | — | — | — | — | S$_1$–S$_5$ = H |
| 22 | | 3 | 3 | — | H | H | 5-F | — | O | — | — | — | — | — | S$_1$ = H |
| 23 | | 3 | 3 | — | H | H | H | — | CH$_2$ | — | — | — | — | — | S$_1$ = H |
| 24 | | 5 | 3 | — | H | H | H | — | — | O | — | — | — | — | S$_1$ = H; position 8 |
| 25 | | 1 | 3 | CH$_2$ | H | H | 7-Cl | — | — | — | — | — | — | — | S$_1$–S$_5$ = H |
| 26 | form | 3 | 3 | — | H | H | 7-F | — | O | — | — | — | — | — | S$_1$ = H |
| 27 | | 1 | 3 | CH$_2$ | H | H | 7-F | — | — | — | — | — | — | — | S$_1$–S$_5$ = H |

-continued

| Comp. no | X | m | Y | R_5 | R_6 | (R_7)n | R | Z | A | S_6 + S_7 | P | T | Q | Remarks |
|---|---|---|---|---|---|---|---|---|---|---|---|---|---|---|
| 28 | 3 | 3 | — | H | H | 7-Cl | — | O | — | — | — | — | — | $S_1$ = H |
| 29 | 3 | 3 | — | H | H | 7-CH_3 | — | O | — | — | — | — | — | $S_1$ = H |
| 30 | 2 | 3 | — | H | H | H | 2-CH_2OCH_3 | — | — | — | — | — | — | $S_1$ = H |
| 31 | 7 | 3 | — | H | H | H | — | — | — | — | N | CH_2 | CH_2 | $S_1$ = H |
| 32 | 1 | 3 | CH_2 | H | H | 6-Cl | — | — | — | — | — | — | — | $S_1$–$S_5$ = H |
| 33 | 3 | 3 | — | H | H | 6-Cl | — | O | — | — | — | — | — | $S_1$ = H |
| 34 | 3 | 3 | — | H | H | 5-CN | — | O | — | — | — | — | — | $S_1$ = H |
| 35 | 1 | 3 | CH_2 | H | H | 5-CN | — | — | — | — | — | — | — | $S_1$–$S_5$ = H |
| 36 | 1 | 3 | CH_2 | H | H | 4-Cl | — | — | — | — | — | — | — | $S_1$–$S_5$ = H |
| 37 | 3 | 3 | — | H | H | 4-Cl | — | O | — | — | — | — | — | $S_1$ = H |
| 38 | 1 | 6 | CH_2 | H | H | H | — | — | — | — | — | — | — | $S_1$–$S_5$ = H |
| 39 | 1 | 5 | CH_2 | H | H | H | — | — | — | — | — | — | — | $S_1$–$S_5$ = H |
| 40 | 1 | 3 | CH_2 | H | H | H | — | — | — | — | — | — | — | $S_1$–$S_4$ = H $S_5$ = CH_3 |
| 41 | 1 | 3 | S | H | H | H | — | — | — | — | — | — | — | $S_4$ = oxo, $S_1$–$S_3$ $S_5$ = H |
| 42 | 6 | 3 | — | H | H | H | — | — | — | oxo | — | — | — | $S_1$ = H |
| 43 | 1 | 3 | S | H | H | H | — | — | — | — | — | — | — | $S_1$–$S_5$ = H |
| 44 | 6 | 3 | — | H | H | H | — | — | — | H_2 | — | — | — | $S_1$ = H |
| 45 | 1 | 4 | CH_2 | H | H | H | — | — | — | — | — | — | — | $S_1$–$S_5$ = H |
| 46 | 1 | 3 | CH_2 | H | H | 6-F | — | — | — | — | — | — | — | $S_1$–$S_5$ = H |
| 47 | 3 | 3 | — | H | H | 6-F | — | O | — | — | — | — | — | $S_1$ = H |
| 48 | 7 | 3 | — | H | H | H | — | — | — | — | N | CH | NH | $S_1$ = H |
| 49 | 1 | 3 | O | H | H | H | — | — | — | — | — | — | — | $S_4$ = oxo, $S_2$ = CH_3, $S_1$ = $S_3$ = $S_5$ = H |
| 50 | 1 | 3 | CH_2 | H | H | H | — | — | — | — | — | — | — | $S_4$ = oxo, $S_1$–$S_3$ $S_5$ = H |
| 51 | form | 3 | 3 | — | H | C_2H_5 | 5-CN | — | O | — | — | — | — | $S_1$ = H |
| 52 | 3 | 3 | — | H | H | H | — | NH | — | — | — | — | — | $S_1$ = H |
| 53 | 7 | 3 | — | H | H | H | — | — | — | — | N | C(CH_3) | NH | $S_1$ = H |
| 54 | 7 | 3 | — | H | H | H | — | — | — | — | NH | N | CH | $S_1$ = H |
| 55 | 7 | 3 | — | H | H | H | — | — | — | — | N | N | NH | $S_1$ = H |
| 56 | 1 | 3 | CH_2 | H | H | 4-F | — | — | — | — | — | — | — | $S_1$–$S_5$ = H |
| 57 | 3 | 3 | — | H | H | 4-F | — | O | — | — | — | — | — | $S_1$ = H |
| 58 | 1 | 3 | CH_2 | H | H | 7-Br | — | — | — | — | — | — | — | $S_1$–$S_5$ = H |
| 59 | 3 | 3 | — | H | H | 7-Br | — | O | — | — | — | — | — | $S_1$ = H |
| 60 | 1 | 3 | O | H | H | H | — | — | — | — | — | — | — | $S_4$ = oxo, $S_1$ = 7-Cl, $S_2$ = $S_3$ = $S_5$ = H |
| 61 | 2 | 3 | — | H | H | 5-F | 2-CH_2OCH_3 | — | — | — | — | — | — | $S_1$ = H |
| 62 | 1 | 3 | CH_2 | H | H | 5,7-F_2 | — | — | — | — | — | — | — | $S_1$–$S_5$ = H |
| 63 | 3 | 3 | — | H | H | 5,7-F_2 | — | O | — | — | — | — | — | $S_1$ = H |
| 64 | 2 | 3 | — | H | H | 7-F | 2-CH_2OCH_3 | — | — | — | — | — | — | $S_1$ = H |
| 65 | 5 | 3 | — | H | H | H | — | — | NH | — | — | — | — | $S_1$ = H; position 5 |
| 66 | 5 | 3 | — | H | H | 5-F | — | — | NH | — | — | — | — | $S_1$ = H; position 5 |
| 67 | 5 | 3 | — | H | H | 7-F | — | — | NH | — | — | — | — | $S_1$ = H; position 5 |
| 68 | 2 | 3 | — | H | H | H | 3-CH_2OCH_3 | — | — | — | — | — | — | $S_1$ = H |
| 69 | 2 | 3 | — | H | H | H | 2-CH_2OCH_3 | — | — | — | — | — | — | $S_1$ = H |
| 70 | 2 | 3 | — | H | H | 5-F | 2-CH_2OCH_3 | — | — | — | — | — | — | $S_1$ = H |
| 71 | 2 | 3 | — | H | H | 5-F | 3-CH_2OCH_3 | — | — | — | — | — | — | $S_1$ = H |
| 72 | 2 | 3 | — | H | H | 7-F | 3-CH_2OCH_3 | — | — | — | — | — | — | $S_1$ = H |
| 73 | 2 | 3 | — | H | H | 7-F | 2-CH_2OCH_3 | — | — | — | — | — | — | $S_1$ = H |
| 74 | 1 | 3 | S | H | H | 5-F | — | — | — | — | — | — | — | $S_4$ = oxo, $S_1$–$S_3$ $S_5$ = H |
| 75 | 2 | 3 | — | H | H | H | 3-CH_2OC_3H_7 | — | — | — | — | — | — | $S_1$ = H |
| 76 | form. | 2 | 3 | — | H | H | 5-F | 3-CH_2OC_3H_7 | — | — | — | — | — | — | $S_1$ = H |
| 77 | 2 | 3 | — | H | H | H | 3-CH_2OCH_2C≡CH | — | — | — | — | — | — | $S_1$ = H |
| 78 | 2 | 3 | — | H | H | 5-F | 3-CH_2OCH_2C≡CH | — | — | — | — | — | — | $S_1$ = H |
| 79 | 2 | 3 | — | H | H | 7-F | 3-CH_2OCH_2C≡CH | — | — | — | — | — | — | $S_1$ = H |
| 80 | 2 | 3 | — | H | H | H | 3-CH_2OCH_2CH_2OCH_3 | — | — | — | — | — | — | $S_1$ = H |
| 81 | 2 | 3 | — | H | H | 5-F | 3-CH_2OCH_2CH_2OCH_3 | — | — | — | — | — | — | $S_1$ = H |
| 82 | 2 | 3 | — | H | H | 7-F | 3-CH_2OCH_2CH_2OCH_3 | — | — | — | — | — | — | $S_1$ = H |
| 83 | 1 | 3 | S | H | H | 5-F | — | — | — | — | — | — | — | $S_1$–$S_5$ = H |
| 84 | 1 | 3 | S | H | H | H | — | — | — | — | — | — | — | $S_2$ = CH_3, $S_1$ = $S_3$–$S_5$ = H |
| 85 | 1 | 3 | S | H | H | H | — | — | — | — | — | — | — | $S_4$ = oxo, $S_2$ = CH_3, $S_1$ = $S_3$ = $S_5$ = H |
| 86 | 7 | 3 | — | H | H | H | — | — | — | — | N | CH | S | $S_1$ = H |
| 87 | 1 | 3 | O | H | H | H | — | — | — | — | — | — | — | $S_4$ = oxo, $S_2$ = CH_3, $S_1$ = $S_3$ = $S_5$ = H |
| 88 | 1 | 3 | O | H | H | H | — | — | — | — | — | — | — | $S_4$ = oxo, $S_2$ = CH_3, $S_1$ = $S_3$ = $S_5$ = H |
| 89 | 1 | 3 | O | H | H | 5-F | — | — | — | — | — | — | — | $S_4$ = oxo, $S_2$ = CH_3, $S_1$ = $S_3$ = $S_5$ = H |
| 90 | 1 | 3 | O | H | H | 5-F | — | — | — | — | — | — | — | $S_4$ = oxo, $S_2$ = CH_3, $S_1$ = $S_3$ = $S_5$ = H |
| 91 | 1 | 3 | O | H | H | 7-F | — | — | — | — | — | — | — | $S_4$ = oxo, $S_2$ = CH_3, $S_1$ = $S_3$ = $S_5$ = H |

-continued

| Comp. no | X | m | Y | $R_5$ | $R_6$ | $(R_7)n$ | R | Z | A | $S_6 + S_7$ | P | T | Q | Remarks |
|---|---|---|---|---|---|---|---|---|---|---|---|---|---|---|
| 92 | | 1 | 3 | O | H | H | 7-F | — | — | — | — | — | — | — | $S_4$ = oxo, $S_2$ = $CH_3$, $S_1 = S_3 = S_5$ = H |
| 93 | | 1 | 3 | O | H | H | H | — | — | — | — | — | — | — | $S_4$ = oxo, $S_2$ = phenyl, $S_1 = S_3 = S_5$ = H |
| 94 | | 1 | 3 | O | H | H | 5-F | — | — | — | — | — | — | — | $S_4$ = oxo, $S_2$ = phenyl, $S_1 = S_3 = S_5$ = H |
| 95 | | 1 | 3 | O | H | H | 7-F | — | — | — | — | — | — | — | $S_4$ = oxo, $S_2$ = phenyl, $S_1 = S_3 = S_5$ = H |
| 96 | | 2 | 3 | — | H | H | H | 3-$CH_2OCH_2CH{=}CH_2$ | — | — | — | — | — | — | $S_1$ = H |
| 97 | | 2 | 3 | — | H | H | 5-F | 3-$CH_2OCH_2CH{=}CH_2$ | — | — | — | — | — | — | $S_1$ = H |
| 98 | | 2 | 3 | — | H | H | 7-F | 3-$CH_2OCH_2CH{=}CH_2$ | — | — | — | — | — | — | $S_1$ = H |
| 99 | | 2 | 3 | — | H | H | H | 2-$CH_2OCH_2C{\equiv}CH$ | — | — | — | — | — | — | $S_1$ = H |
| 100 | | 2 | 3 | — | H | H | 5-F | 2-$CH_2OCH_2C{\equiv}CH$ | — | — | — | — | — | — | $S_1$ = H |
| 101 | form. | 2 | 3 | — | H | H | 7-F | 2-$CH_2OCH_2C{\equiv}CH$ | — | — | — | — | — | — | $S_1$ = H |
| 102 | | 1 | 3 | O | H | H | H | — | — | — | — | — | — | — | $S_4$ = oxo, $S_2$ = $C_3H_7$, $S_1 = S_3 = S_5$ = H |
| 103 | | 1 | 3 | O | H | H | 5-F | — | — | — | — | — | — | — | $S_4$ = oxo, $S_2$ = $C_3H_7$, $S_1 = S_3 = S_5$ = H |
| 104 | | 1 | 3 | O | H | H | 7-F | — | — | — | — | — | — | — | $S_4$ = oxo, $S_2$ = $C_3H_7$, $S_1 = S_3 = S_5$ = H |
| 105 | | 1 | 3 | O | H | H | H | — | — | — | — | — | — | — | $S_4$ = oxo, $S_2 = S_5$ = $CH_3$, $S_1 = S_3$ = H |
| 106 | | 1 | 3 | O | H | H | 5-F | — | — | — | — | — | — | — | $S_4$ = oxo, $S_2 = S_5$ = $CH_3$, $S_1 = S_3$ = H |
| 107 | | 1 | 3 | O | H | H | 7-F | — | — | — | — | — | — | — | $S_4$ = oxo, $S_2 = S_5$ = $CH_3$, $S_1 = S_3$ = H |
| 108 | | 1 | 3 | O | H | H | H | — | — | — | — | — | — | — | $S_4$ = oxo, $S_2$ = benzyl, $S_1 = S_3 = S_5$ = H |
| 109 | | 1 | 3 | O | H | H | 5-F | — | — | — | — | — | — | — | $S_4$ = oxo, $S_2$ = benzyl, $S_1 = S_3 = S_5$ = H |
| 110 | | 1 | 3 | O | H | H | 7-F | — | — | — | — | — | — | — | $S_4$ = oxo, $S_2$ = benzyl, $S_1 = S_3 = S_5$ = H |
| 111 | | 2 | 3 | — | H | H | H | 3-$CH_2OCH_2C{\equiv}CCH_3$ | — | — | — | — | — | — | $S_1$ = H |
| 112 | | 2 | 3 | — | H | H | H | 2-$CH_2OCH_2C{\equiv}CCH_3$ | — | — | — | — | — | — | $S_1$ = H |
| 113 | | 2 | 3 | — | H | H | 5-F | 2-$CH_2OCH_2C{\equiv}CCH_3$ | — | — | — | — | — | — | $S_1$ = H |
| 114 | | 1 | 3 | O | H | H | H | — | — | — | — | — | — | — | $S_4$ = oxo, $S_2 = S_3$ = $CH_3$, $S_1 = S_5$ = H |
| 115 | | 1 | 3 | O | H | H | 5-F | — | — | — | — | — | — | — | $S_4$ = oxo, $S_2 = S_3$ = $CH_3$, $S_1 = S_5$ = H |
| 116 | | 2 | 3 | — | H | H | H | 3-$CH_2OCH_3$ | — | — | — | — | — | — | $S_1$ = H |
| 117 | | 2 | 3 | — | H | H | 5-F | 3-$CH_2OCH_3$ | — | — | — | — | — | — | $S_1$ = H |
| 118 | | 2 | 3 | — | H | H | 5-F | 3-$CH_2OCH_3$ | — | — | — | — | — | — | $S_1$ = H |
| 119 | | 2 | 3 | — | H | H | H | 3-$CH_2OCH_3$ | — | — | — | — | — | — | $S_1$ = H |
| 120 | | 1 | 3 | O | H | H | H | — | — | — | — | — | — | — | $S_4$ = oxo, $S_2 = S_5$ = $CH_3$, $S_1 = S_3$ = H |
| 121 | | 1 | 3 | O | H | H | 5-F | — | — | — | — | — | — | — | $S_4$ = oxo, $S_2 = S_5$ = $CH_3$, $S_1 = S_3$ = H |
| 122 | | 1 | 3 | O | H | H | 5-F | — | — | — | — | — | — | — | $S_4$ = oxo, $S_2 = S_5$ = $CH_3$, $S_1 = S_3$ = H |
| 123 | | 1 | 3 | O | H | H | H | — | — | — | — | — | — | — | $S_4$ = oxo, $S_2 = S_5$ = $CH_3$, $S_1 = S_3$ = H |
| 124 | | 1 | 3 | O | H | H | 5-F | — | — | — | — | — | — | — | $S_4$ = oxo, $S_1$ = 7-Cl, $S_2 = S_3 = S_5$ = $CH_3$ |
| 125 | | 1 | 3 | O | H | H | 5-F | — | — | — | — | — | — | — | $S_4$ = oxo, $S_1$ = H, $S_2 = S_3 = S_5$ = $CH_3$ |
| 126 | | 2 | 3 | — | H | H | 5-F | 3-$CH_2OCH_3$ | — | — | — | — | — | — | $S_1$ = H |

*$R_7$ is linked to position 7 of the indole group

| Comp. no | Salt or free base | MP (° C.) | $[\alpha]_D^{25}$ (in methanol) |
|---|---|---|---|
| 1 | fumarate | 192–4 | — |
| 2 | 2-HCl | 239–41 | — |
| 3 | free base | 203–4 | — |
| 4 | " | 170–1 | — |
| 5 | 3. fumarate | 98 | — |
| 6 | free base | 175–6 | — |
| 7 | 4/3. fumarate | 140–3 | — |
| 8 | free base | 189–90 | — |
| 9 | fumarate | 200–1 | — |
| 10 | 3/2. fumarate | 190–1 | — |
| 11 | ½. fumarate | 210–2 (dec.) | — |
| 12 | free base | 165–7 | — |
| 13 | free base | 70–1 | — |
| 14 | fumarate | 208 | — |
| 15 | free base | amorph | — |
| 16 | 2. fumarate | amorph | — |
| 17 | free base | amorph | — |
| 18 | fumarate | >225 (dec.) | — |
| 19 | fumarate | >170 (dec.) | — |
| 20 | free base | amorph | — |
| 21 | ½. fumarate | >245 (dec) | — |
| 22 | ½. fumarate | >165 (glass) | — |
| 23 | free base | 176–7 | — |
| 24 | free base | amorph | — |
| 25 | ½. fumarate | amorph | — |
| 26 | ¾. fumarate | amorph | — |
| 27 | ½. fumarate | >240 (dec) | — |
| 28 | 4/5. fumarate | amorph | — |
| 29 | " | amorph | — |
| 30 | 3/2. fumarate | glass | — |
| 31 | 5/4. fumarate | 188–190 | — |
| 32 | ½. fumarate | >230 (dec) | — |
| 33 | fumarate | amorph | — |
| 34 | fumarate | 150–2 | — |
| 35 | ½. fumarate | 247–8 (dec) | — |
| 36 | ½. fumarate | >240 (dec) | — |
| 37 | fumarate | amorph | — |
| 38 | HCl | amorph | — |
| 39 | HCl | amorph | — |
| 40 | HCl | 220–4 | — |
| 41 | HCl | >250 (dec) | — |
| 42 | ½. fumarate | 214–7 (dec) | — |
| 43 | ½. fumarate | 240–3 | — |
| 44 | ½. fumarate | 220–2 (dec) | — |
| 45 | HCl | amorph | — |
| 46 | fumarate | 223–5 | — |
| 47 | 2/3. fumarate | 200–2 | — |
| 48 | free base | glass | — |
| 49 | free base | 196–7 | — |
| 50 | free base | 181–2 | — |
| 51 | ½. fumarate | 138.5–41 | — |
| 52 | free base | 190–5 (dec) | — |
| 53 | free base | glass | — |
| 54 | free base | glass | — |
| 55 | free base | glass | — |
| 56 | ½. fumarate | 185–6 | — |
| 57 | fumarate | 210–1 (dec) | — |
| 58 | 2. fumarate | amorph | — |
| 59 | free base | amorph | — |
| 60 | ½. fumarate | >250 | — |
| 61 | fumarate | glass | — |
| 62 | ½. fumarate | 245–7 | — |
| 63 | 3/2. fumarate | 175–8 | — |
| 64 | fumarate | glass | — |
| 65 | free base | 220–4 (dec) | — |
| 66 | free base | 234–6 (dec) | — |
| 67 | free base | >280 | — |
| 68 | HCl | glass | — |
| 69 | fumarate | glass | +28 (free base), R-conf. |
| 70 | fumarate | glass | +28 (free base), R-conf. |
| 71 | fumarate | glass | — |
| 72 | fumarate | glass | — |
| 73 | fumarate | glass | +25 (free base), R-conf. |
| 74 | free base | 212.5–14.5 | — |
| 75 | fumarate | glass | — |
| 76 | fumarate | glass | — |
| 77 | fumarate | glass | — |
| 78 | fumarate | glass | — |
| 79 | fumarate | glass | — |
| 80 | fumarate | glass | — |
| 81 | fumarate | glass | — |
| 82 | fumarate | glass | — |
| 83 | fumarate | amorph | — |
| 84 | free base | amorph | — |
| 85 | free base | amorph | — |
| 86 | ½. fumarate | 218–20 | — |
| 87 | free base | glass | −26 R-conf. |
| 88 | free base | glass | +27 S-conf. |
| 89 | free base | glass | −24 R-conf. |
| 90 | free base | glass | +24 S-conf. |
| 91 | free base | 184–5 | −25 R-conf. |
| 92 | free base | 181–3 | +25 S-conf. |
| 93 | free base | glass | — |
| 94 | free base | glass | — |
| 95 | free base | glass | — |
| 96 | free base | 70–3 | — |
| 97 | free base | 73–5 | — |
| 98 | fumarate | glass | — |
| 99 | fumarate | glass | +39 (free base), R-conf. |
| 100 | fumarate | glass | +36 (free base), R-conf. |
| 101 | fumarate | glass | +37 (free base), R-conf. |
| 102 | free base | 158–60 | — |
| 103 | free base | 181–2 | — |
| 104 | free base | 174–6 | — |
| 105 | free base | glass | — |
| 106 | free base | glass | — |
| 107 | free base | glass | — |
| 108 | free base | glass | — |
| 109 | free base | 207–10 (dec) | — |
| 110 | free base | 197–9 (dec) | — |
| 111 | fumarate | glass | — |
| 112 | fumarate | glass | +31 (free base), R-conf |
| 113 | fumarate | glass | +31 (free base), R-conf |
| 114 | free base | 191–4 | — |
| 115 | free base | 190–2 | — |
| 116 | free base | amorph | 0 S-conf. |
| 117 | fumarate | amorph | S-conf. |
| 118 | free base | amorph | R-conf. |
| 119 | free base | amorph | 0 R-conf. |
| 120 | free base | amorph | −31 R-conf. |
| 121 | free base | amorph | −28 R-conf. |
| 122 | free base | amorph | +28 S-conf. |
| 123 | free base | amorph | +32 S-conf. |
| 124 | free base | amorph | — |
| 125 | free base | amorph | — |
| 126 | fumarate | amorph | −2 R-conf. |

The invention claimed is:

1. A compound of the formula (I):

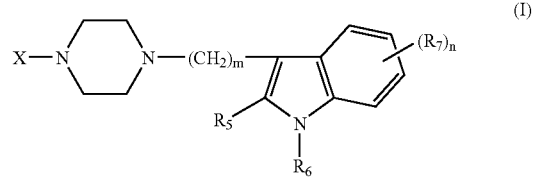

wherein:
X is 1) a group of the formula

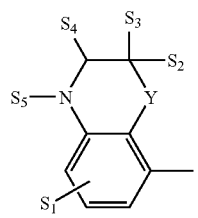
(1)

wherein
- $S_1$ is hydrogen or halogen,
- $S_2$ and $S_3$ are independently hydrogen, alkyl (1–6C), phenyl or benzyl,
- $S_4$ represents two hydrogen atoms or an oxo group,
- $S_5$ is H or alkyl (1–4C), and
- Y is $CH_2$, O or S, and
- m has the value 2 to 6;
- n has the value 0–2;
- $R_5$ and $R_6$ are independently H or alkyl (1–3C); or $R_5+R_6$ represent a group $—(CH_2)—_p$ wherein p has the value 3–5, and
- $R_7$ is alkyl (1–3C), alkoxy (1–3C), halogen or cyano; or $R_6+R_7$ ($R_7$ at position 7 of the indole group) represent a group $—(CH_2)_q$ wherein q has the value 2–4, an enantiomer thereof, or a salt of any of the foregoing.

2. A compound as claimed in claim 1, wherein m is 3, $R_5=R_6=H$, n is 0 or 1, and $R_7$ is 5-fluoro, an enantiomer thereof, or a salt of any of the foregoing.

3. A method for preparing a compound, an enantiomer thereof, or a salt of any of the foregoing as claimed in claim 1, comprising reacting a compound having formula (II)

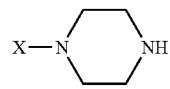
(II)

under basic conditions with a compound having formula (III)

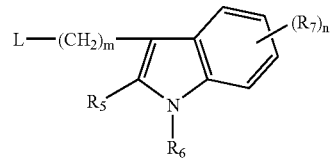
(III)

in which formulae the symbols having the meanings given in claim 1, and L is a leaving group, to yield the compound, the enantiomer thereof, or the salt of any of the foregoing as claimed in claim 1.

4. A pharmaceutical composition comprising at least one compound as claimed in claim 1, an enantiomer thereof, or a salt of any of the foregoing and at least one auxiliary substance.

5. A method of preparing a composition as claimed in claim 4, comprising mixing the at least one compound, an enantiomer thereof, or a salt of any of the foregoing with the at least one auxiliary substance.

6. A method of treating at least one central nervous system disorder in a human or animal patient in need of such treating, comprising administering at least one compound as claimed in claim 1, an enantiomer thereof, a salt of any of the foregoing, or a combination of the foregoing to the patient in an amount effective for the treating, wherein the at least one central nervous system disorder is chosen from anxiety disorders, depression, Parkinson's disease, and schizophrenia.

7. The method of claim 6, in which the at least one central nervous system disorder is chosen from schizophrenia.

* * * * *

UNITED STATES PATENT AND TRADEMARK OFFICE
CERTIFICATE OF CORRECTION

PATENT NO. : 7,067,513 B1　　　　　　　　　　　　　　　　　　　　　　　Page 1 of 1
APPLICATION NO. : 10/069256
DATED : June 27, 2006
INVENTOR(S) : Roelof Van Hes et al.

It is certified that error appears in the above-identified patent and that said Letters Patent is hereby corrected as shown below:

Column 17, line 29, before the letter "m" please insert --$S_1=S_3=S_5=H$, $S_4$=oxo and $S_2=CH_3$,--.

Signed and Sealed this

Twenty-seventh Day of February, 2007

JON W. DUDAS
*Director of the United States Patent and Trademark Office*